United States Patent [19]

Cavazza

[11] 4,439,438
[45] Mar. 27, 1984

[54] ESTERS OF ACYL-CARNITINES, PROCESS FOR PREPARING SAME AND PHARMACEUTICAL COMPOSITIONS CONTAINING SUCH ESTERS

[76] Inventor: Claudio Cavazza, 35, Via Marocco, 00144 Rome, Italy

[21] Appl. No.: 382,319

[22] Filed: May 26, 1982

Related U.S. Application Data

[63] Continuation of Ser. No. 142,503, Apr. 21, 1980, abandoned.

[30] Foreign Application Priority Data

Apr. 23, 1979 [IT] Italy ................... 48816 A/79

[51] Int. Cl.³ .................... A61K 31/44; C07C 211/72
[52] U.S. Cl. .................... 424/263; 424/311; 424/312; 546/300; 560/170
[58] Field of Search .............. 560/170; 424/311, 312, 424/263; 546/300

[56] References Cited

U.S. PATENT DOCUMENTS 4,032,641 6/1977 Chibata et al. ............... 424/260

FOREIGN PATENT DOCUMENTS 2388556 11/1978 France .
37-5174 6/1962 Japan .
38-24 1/1963 Japan .

OTHER PUBLICATIONS

Riuniti, Chem. Abst., vol. 92, #215769(t) (1980).
Mino et al, Chem. Abst., vol. 71, #151495(f) (1972).
Strack et al, Chem. Abst., vol. 64, #19398(f) (1966).

*Primary Examiner*—James H. Reamer
*Attorney, Agent, or Firm*—Ladas & Parry

[57] ABSTRACT

Novel esters of acyl-carnitines having general formula

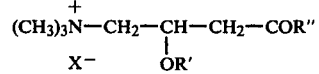

wherein R' is acetyl, propionyl, butyryl (unsubstituted or halogen-substituted), isobutyryl, β-hydroxy butyryl, acetoacetyl, pantothenyl and linoleyl, and R" is an alkoxy radical either unsubstituted alkoxy, typically: isobutyloxy or substituted alkoxy, typically: trichloroethyloxy) are therapeutically effective in the treatment of myocardial hypocontractility and as antidepresants.

5 Claims, No Drawings

ESTERS OF ACYL-CARNITINES, PROCESS FOR PREPARING SAME AND PHARMACEUTICAL COMPOSITIONS CONTAINING SUCH ESTERS

This is a continuation, of application Ser. No. 142,503 filed Apr. 21, 1980, now abandoned.

The present invention relates to a novel class of esters of acyl-carnitines, the processes for preparing same and the pharmaceutical compositions containing such esters.

More particularly, the present invention relates to esters of acyl-carnitines represented by the general formula (I):

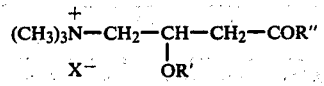

wherein $X^-$ is a halogen anion, preferably $Cl^-$;

R' is: acetyl; halogen-substituted acetyl (e.g. chloro-acetyl, dichloro-acetyl, bromo-acetyl and the like); propionyl; halogen-substituted propionyl (e.g. bromopropionyl); butyryl; halogen-substituted butyryl (e.g. chlorobutyryl); isobutyryl; β-hydroxy butyryl; acetoacetyl, linoleyl and pantothenyl; and R'' is: methoxy, ethoxy, propyloxy, butyloxy (provided that R' is not acetyl) isopropyloxy, isobutyloxy, trichloroethyloxy, trifluoroethyloxy, 3-carbethoxy-2-propyloxy, 3-pyridylmethoxy, 2-diethylaminoethoxy, 2-acetamido-3-methyl-butyloxy, 2-acetamido-4-methyl-pentyloxy, 2-acetamido-3-methylpentyloxy and 4-hydroxymethyl-5-hydroxy-6-methyl pyrid- 3-yl methoxy radicals.

It has been found that the compounds of the present invention have interesting pharmacologic properties and therefore can exhibit useful therapeutic applications.

In particular: the esters of formula (I) have shown to be endowed with an important inotropic effect due to the prolonging of action and to the fact that they are devoid of effects which might depress myocardial excitability. It is maintained and no theoretical interpretation is intended here, that this is due to the capability of the ester bond to protect acyl carnitine from rapid metabolic degradation and the rapid fall in blood levels. The compounds exert cerebral neurochemical effects consisting in changes of central serotoninergic activities.

The compounds can therefore be therapeutically used (a) for the treatment of myocardial hypocontractility unaccompanied by rhythm disorders, as for instance in cardiogenic shock determined by the primary absence of contractile force;

(b) as antidepressants in cases of disturbed sleep.

In accordance with the invention, the esters of formula (I) are prepared starting from carnitine hydrochloride by following two distinct synthesis routes depending on whether either the hydroxyl group of carnitine is firstly converted into an acyl group and then the carboxyl group of carnitine is esterified (Process A) or the carboxyl group of carnitine is firstly esterified and then the hydroxyl group of carnitine is converted into an acyl group (Process B).

More specifically:

Process A comprises the following steps:

(a) adding to a carnitine solution in a solvent selected from the group consisting of organic acids and the corresponding anhydrides an acyl halogenide of formula R'X wherein R' has the aforementioned meaning and X is a halogen atom, and keeping the temperature of the thus obtained mixture at about 4–48 hours, thus obtaining the corresponding acyl-derivative of carnitine;

(b) isolating the acyl-derivative of carnitine by adding to the mixture of step (a) a precipitating agent and by purifying through repeated crystallizations;

(c) reacting the acyl-derivative of carnitine of step (b) with an excess of a halogenating agent at about 25°–60° C. for about 0.3–24 hours and removing the excess of the halogenating agent, thus obtaining the corresponding acid halogenide of the acyl-derivative of carnitine;

(d) condensing the acid halogenide of the acyl-derivative of carnitine of step (c) with an alcohol of formula R''H wherein R'' has the aforementioned meaning, keeping the thus obtained mixture under stirring at room temperature for about 2–24 hours, thus obtaining the ester (I); and (e) isolating the ester (I) by drying the mixture of step (d) and repeatedly crystallizing from organic solvents.

Process A is illustrated in the following synthesis scheme 1:

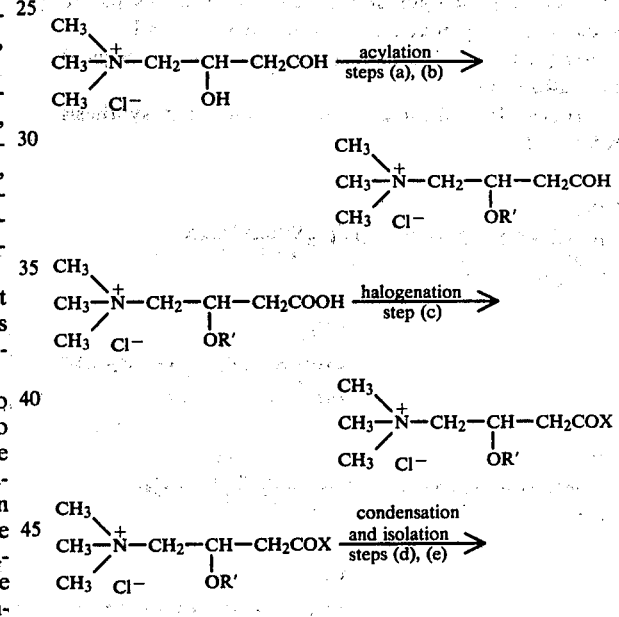

In the step (a), the organic acid or the corresponding anhydride wherein carnitine is dissolved, are preferably halogenated. Particularly preferred solvents are trifluoroacetic acid and trichloroacetic acid.

In the step (b), the precipitating agent is selected from the class of esters and ketones, ethyl ether being particularly preferred. In the purification step by repeated crystallizations of the carnitine acyl-derivative, ethanol, acetone, isopropanol and acetonitrile are preferably used.

In the step (c), the halogenation is preferably a chloruration. Preferably, the chloruration is carried out with thionyl chloride at about 40°–50° C. for about 20–40 minutes, or with oxalyl chloride at room temperature for about 3–5 hours, or with phosphorous pentachloride in an organic medium (e.g. chloroform) at room temperature for about 22-26 hours.

In the step (d), the condensation is carried out by adding to the selected alcohol the halogenides of the carnitine acyl-derivatives as such or dissolved in an organic anhydrous, inert solvent (e.g. chloroform or methylene chloride).

Process B comprises the following steps:

(a') suspending carnitine in the desired alcohol R''H;

(b') reacting the suspension of step (a') with an anhydrous inorganic acid until complete dissolution of the suspended carnitine, thus obtaining the corresponding ester;

(c') reacting the ester of step (b') with an excess of acyl halogenide of formula R'X wherein R' has the aforementioned meaning and X is a halogen atom, keeping the thus obtained mixture at a temperature of about 25°-40° C. for about 2-24 hours, thus obtaining the corresponding ester of the acyl-derivative of carnitine of formula (I);

(d') treating the mixture comprising therein the ester of formula (I) with an organic solvent in which the excess of acyl halogenide is soluble in order to separate such acyl halogenide axcess from the ester; and (e') purifyring the ester of formula (I) by repeated crystallization.

Process B is illustrated in the following synthesis scheme 2:

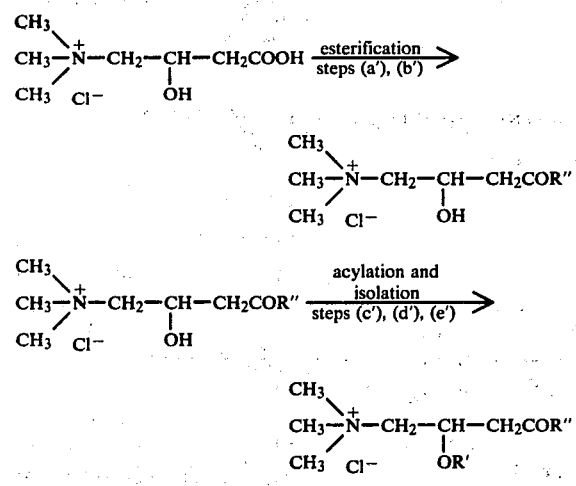

In the step (b'), the esterification is preferably carried out by either bubbling into the carnitine suspension in alcohol a gaseous HCl stream until the suspended phase disappears, or adding to the carnitine suspension in alcohol concentrated sulphuric acid and heating the resulting mixture up to reflux temperature until the suspended phase disappears.

In the step (c'), the acyl halogenide is usually an acyl chloride (e.g. acetyl, propionyl, butyryl chloride and the like). The excess of acyl chloride with respect to the carnitine ester obtained in the step (b') is such that the molar ratio of the two compounds ranges between 3:1 and 1.5:1, and is preferably 2:1.

The following non-limiting examples illustrate the preparation of some of the esters and amides of the present invention.

EXAMPLE 1

Preparation of the acetyl carnitine isopropyl ester (Process A)

Preparation of acetyl carnitine chloride 2 grams of carnitine chloride were dissolved in 20 ml of glacial acetic acid, and acetyl chloride (10 ml) was added thereto. The reaction mixture was kept at room temperature for 48 hours. The excess of acetyl chloride and the solvent were removed under vacuum, by heating on a water bath at 50° C. The residue was crystallized from isopropanol-ethyl ether, and a pure product was thus obtained.

| M.P. | 188° C. (dec.) | | | | |
|---|---|---|---|---|---|
| yield | 90% | C | H | N | Cl |
| Elem. An. C$_7$H$_{16}$ClNO$_3$ | calculated | 42.53 | 8.16 | 7.09 | 17.94 |
| | found | 42.39 | 8.18 | 7.20 | 17.63 |
| NMR: | | | | | |

$\partial$ 5.50 (M,1H, —CH—); 3.82 (d,2H, $\overset{\diagdown}{\underset{\diagup}{\overset{+}{N}}}$—CH$_2$—);
             |
            OCO 3.20 (s, 9H, (CH$_3$)$_3\overset{+}{N}$—); 2.68 (d,2H, —CH$_2$—CO);

2.02 (s,3H,COCH$_3$); D$_2$O

Preparation of the acid chloride of acetyl carnitine chloride

Acetyl carnitine chloride (2 g; 0.01 moles), prepared as previously indicated was suspended in oxalyl chloride (5 cc). The reaction mixture was kept at room temperature for 4 hours. The oxalyl chloride excess was then evaporated under vacuum. The residue was washed (3 times) with small volumes (10 cc) of anhydrous ethyl ether and kept under vacuum until complete removal of the solvent. The residue was used as such in the next reaction.

Preparation of acetyl carnitine isopropyl ester

The previously obtained acid chloride (2 grams) was reacted with an excess of isopropanol (8 cc) at room temperature under magnetic stirring for 3 hours. Ethyl ether (400 cc) was then added to the reaction mixture. Thereupon, a thick oil deposited. The mother liquors were decanted and the precipitate was taken up with anhydrous CH$_3$CN. Unreacted acetyl carnitine separated from the clear solution and was filtered off. The CH$_3$CN was evaporated. The residue, dried over P$_2$O$_5$, was found to be the desired product.

| yield | 75% | C | H | N |
|---|---|---|---|---|
| Elem. An. C$_{12}$H$_{24}$ClNO$_4$ | calculated | 51.15 | 8.58 | 4.97 |
| | found | 51.00 | 8.55 | 4.81 |
| NMR: | | | | |

$\partial$ 5.6 (m,1H—CH—); 5.2 (m,1H, —CH$\underset{\diagdown CH_3}{\overset{\diagup CH_3}{\phantom{X}}}$);
              |
             OCO 3.7 (d,2H, $\overset{\diagdown}{\underset{\diagup}{N}}$—CH$_2$—); 3.2 (s,9H,N (CH$_3$)$_3$);

2.7 (d,2H, —CH$_2$—CO); 2.1 (s,3H, —COCH$_3$);

1.3 (d,6H,CH(CH₃)(CH₃)); CD₃CN

EXAMPLE 2

Preparation of the ester of acetyl carnitine chloride with ethyl β-hydroxy butyrate (Process A)

Preparation of ethyl ester of 3-hydroxy butyric acid

A solution of 3-hydroxy butyric acid (2 grams; 0.02 moles) in absolute ethanol (50 cc) and concentrated sulfuric acid (2 cc) was kept at reflux temperature for 15 hours. The ethanol was evaporated and the residue was taken up with water and ethyl ether. The organic phase was washed with a diluted NaHCO₃ solution and then with aqueous saturated NaCl solution until neutrality was reached. The solution was then dried (over anhydrous Na₂SO₄), filtered and evaporated until a residue was obtained which was found to be the ethyl ester of 3-hydroxy butyric acid. This compound was used as such in the next reaction.

Preparation of the ester of acetyl carnitine with ethyl β-hydroxy butyrate

To a solution of the acid chloride of acetyl carnitine prepared as disclosed in Example 1 (0.01 moles in 30 cc of anhydrous CH₂Cl₂) the ethyl ester of β-hydroxy butyric acid previously prepared and dissolved in 20 cc of anhydrous CH₂Cl₂ was added. The reaction mixture was kept under stirring at room temperature for 5 hours. Then, ethyl ether (100 cc) was added thereto. Thereupon, a thick oil deposited. The solution was decanted and the residue washed first with ethyl ether (50 cc) and then taken up with anhydrous CH₃CN. From the solution crystals of acetyl carnitine separated, which were filtered off. The filtrate was again precipitated with ethyl ether. The deposited substance was taken up with anhydrous CH₃CN, filtered and evaporated. A thick oil was obtained which was dried in the presence of P₂O₅.

| yield | 60% | C | H | N |
|---|---|---|---|---|
| Elem. An. C₁₅H₂₈ClNO₆ | calculated | 50,77 | 7,95 | 10,02 |
| | found | 50,31 | 7,63 | 10,17 |

NMR:

∂ 5,6 (m, 1H, —N—CH₂—CH); —O—

5,2 (m,1H, —CH—O—CO—);

4,1 (q,2H, O—CH₂—CH₃); 3,8 (d, 2H, —N—CH₂—);

3,2 (s,9H, N (CH₃)₃);

2,7 (m,4H, —CH₂COO—CH(CH₂COO));

2,1 (s,3H,CH₃CO); 1,3 (m, 6H, CH₃, CH₃—CH₂); DMSO CH

EXAMPLE 3

Preparation of propionyl carnitine isopropyl ester (Process B)

Preparation of carnitine isopropyl ester

Carnitine (1.98 grams; 0.01 moles) was suspended in isopropanol (10 cc). Anhydrous, gaseous hydrochloric acid was bubbled in the suspension at 5° C. until saturation was reached. Then, the solution was kept at 60° C. for 3 hours. Thesolution was then concentrated under vacuum and the residue crystallized with isopropanol-ethyl ether:

| M.P. | 145° C.–150 C. | | | | |
|---|---|---|---|---|---|
| yield | 65% | C% | H% | N% | Cl% |
| Elem. An. C₁₀H₂₂ClNO₃ | calculated | 50.10 | 9.25 | 5.84 | 14.79 |
| | found | 49.65 | 9.21 | 5.46 | 14.49 |

NMR:

∂ 5.1 (m,1H, O—CH(CH₃)(CH₃)); 4.5 (covered, CH); OH 3.5 (d, 2H, —N⁺—CH₂—); 3.2 (s,9H, N (CH₃)₃);

2.7 (d, 2HCH₂CO); 1.3 (d, 6H,CH(CH₃)(CH₃)); D₂O

Preparation of propionyl carnitine isopropyl ester

To the carnitine isopropyl ester (1 g; 0.005 moles) previously obtained, propionyl chloride (1 cc; 0.01 moles) was added. The resulting mixture was kept under stirring at room temperature until complete dissolution of carnitine isopropyl ester in 24 hours was reached. To the solution thus obtained ethyl ether was then added, whereupon a thick oil precipitated which, repeatedly taken up with isopropanol-ethyl ether, furnished a compound having the following characteristics (yield: 75%):

| | C | H | N | Cl |
|---|---|---|---|---|
| Elem. An. C₁₃H₂₆ClNO₄ calculated | 52.78 | 8.86 | 4.74 | 11.98 |
| found | 52.65 | 8.78 | 4.65 | 12.02 |

NMR:

∂ 5.7 (m, 1H, CH); 4.9 (m, 1H,CH(CH₃)(CH₃)); O 3.8 (d, 2H, —N⁺—CH₂); 3.2 (s, 9H, N (CH₃)₃);

2.7 (d,2H,CH—CH₂CO); 2.5 (q,2H,CH₂CH₃);

-continued 1.2 (m,9H,CH$_2$—CH$_3$, 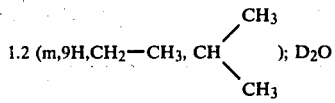); D$_2$O

EXAMPLE 4

Preparation of isobutyryl carnitine isobutyl ester (Process A)

Preparation of isobutyryl carnitine

To a solution of carnitine (3 grams; 0.015 mole) in trifluoroacetic acid (5 cc), isobutyryl chloride (10 cc; 0.096 moles) was added dropwise. The resulting mixture was kept at 45° C. for 4 hours, acetone was added thereto and the residual carnitine was filtered off. Anhydrous ethyl ether was added to the solution and the desired product (2 grams; yield 66%) was obtained by precipitation.

| M.P. | 114-116° C. |
|---|---|
| TLC | eluent CHCl$_3$,CH$_3$OH,NH$_3$ 50:30:8 |
| NMR | ∂ 5.7 (m,1H, —CH—); 3.8 (d,2H, $\overset{+}{\underset{/}{\text{—N}}}$—CH$_2$—);<br>OCO<br><br>3.23 (s,9H, (CH$_3$)$_3\overset{+}{\text{N}}$) 2.8 (d,2H, —CH$_2$COO—);<br><br>2.6 (m,1H, —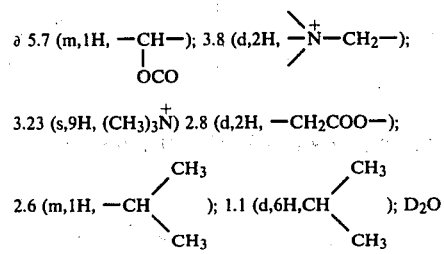); 1.1 (d,6H,CH ); D$_2$O |

Preparation of isobutyryl carnitine acid chloride

Isobutyryl carnitine (2.7 grams; 0.01 moles) obtained as previously indicated was suspended in oxalyl chloride (4.5 cc; 0.05 moles) and the suspension kept under stirring at room temperature for 4 hours. Subsequently, the suspension was diluted with anhydrous ethyl ether and concentrated under vacuum. The residue was treated twice with anhydrous ethyl ether and the raw product thus obtained (2.5 grams; 0.009 moles) was used in the next reaction.

Preparation of isobutyryl carnitine isobutyl ester

Isobutanol (15 cc) was added at 0° C. under stirring to the isobutyryl carnitine acid chloride (2.5 grams; 0.009 moles) previously prepared.

The reaction mixture was kept under stirring for 1 hour still keeping the temperature at about 0° C. The mixture was then concentrated, the residue dissolved in anhydrous acetone and the resulting solution was neutralized with anhydrous Na$_2$CO$_3$. The mixture was filtered and brought to dryness. The residue (2.3 grams; 0.007 moles) was found to be isobutyril carnitine isobutyl ester (yield 70%).

NMR ∂ 5.7 (m,1H, —);
OCO

-continued 3.9 (m,4H, $\overset{+}{\underset{/}{\text{—N}}}$—CH$_2$—, —CH$_2$O—);

2.9 (d,2H, —CH$_2$COO); 2.6 (m,1H,COCH);

1.9 (m,1H,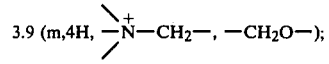); 1.1 (d,6H,COCH );

0.9 (d,6H, CH$_2$—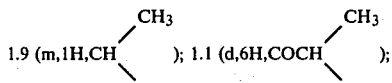); D$_2$O

PHARMACOLOGIC EFFECTS

The pharmacologic effects of the compounds forming the subject matter of the invention were investigated by means of the following techniques.

(a) Acute Toxicity (LD$_{50}$)

The method used was that described by C. S. Weil in "Tables for convenient calculation of median-effect dose (LD$_{50}$ or ED$_{50}$) and instructions on their use," Biometrics, 249-263, 1952.

The tolerance of the compounds under investigation was studied after either i.p. or oral administration to rats. The results show that the compounds under investigation are excellently tolerated (see Table).

(b) Inotropic effect

Rabbit hearts isolated by Langendorff's method were perfused in a Ringer solution oxygenated at 38.2° C. The isometric concentrations, ECG and coronary flow were recorded using a "Battaglia-Rangoni" polygraph.

Metabolic damage in the heart muscle was induced by removing the oxygen from the perfusion liquid until contractile force was reduced by 80%.

In these conditions of prolonged anoxia myocardial aerobic glycolysis was slowed down, accompanied by accumulation of catabolic acids due to storage of pyruvic acid and its conversion to lactic acid which cannot be utilized owing to the depression of the pyridinic enzymes, such as lacticodehydrogenase. This affects anaerobic glycolysis involving an ever increasing number of enzymes, with a progressive and increasingly more critical exhaustion of the myocardium.

Thus there is a whole series of cardiac muscle fatigue levels recorded by the pattern of the parameters taken into account i.e. contractile force, coronary output, heart rate and cardiac rhythm. As soon as the contractile force was reduced by 80%, the perfusion liquid was once again oxygenated without adding other compounds (controls) or with the addition of the compounds under investigation at various concentrations.

The contractile force of the heart was investigated and showed a positive inotropic effect at 10 minutes following interruption of the period of anoxia (restoration of the myocardium).

The results of Student's "t" test showed that the compounds under investigation induce a statistically significant positive inotropic effect versus controls. The Table illustrates the increased percentage values versus controls.

(c) Effect on CNS (central nervous system)

The method used was that described by Irwin S., Nodin J. H., Siegler P. E., in "Animal and Clinical Pharmacologic techniques in Drug Evaluation," Year Book Medical Publ., Chicago, 1964, 36.

The determination of cerebral serotonin (5-HT) and 5-hydroxyindolacetic acid (5-HIAA) was carried out by means of the technique of Ansell and Beeson, Anal. Biochem. 23, 196–206 (1968) Maickel and Cox Int. J. Neuropharmacol. 7—275–281 (1968) using rat brain removed at 1 hour following i.p. injection of 50–100 mg of the compounds under investigation. See Table.

TABLE

Pharmacologic activity of some carnitine esters.
$LD_{50}$ i.p. and oral in mice, inotropic effect on isolated rabbit heart
Cerebral concentrations of 5-HT and 5-HIAA in the rat.

| $(CH_3)_3\overset{+}{N}$—$CH_2$—CH—$CH_2$—COR″ <br> \| <br> OR′ | $LD_{50}$ mg $Kg^{-1}$ i.p. | os | Inotropic effect (dose $10^{-5}$ g$l^{-1}$) % of controls | Cerebral content of 5-HT[a] % of controls | 5-HIAA[a] % of controls |
|---|---|---|---|---|---|
| R′ = acetyl | | | | | |
| R″ = trichloroethyloxy | 1500 | 4000 | +70 | +15 | −25 |
| = isopropyloxy | 700 | 2500 | +80 | +18 | −29 |
| = 3-carbethoxy-2-propyloxy | 600 | 2400 | +90 | +25 | −30 |
| R′ = propionyl | | | | | |
| R″ = isopropyloxy | 800 | 2700 | +75 | +31 | −29 |
| = 3-carbethoxy-2-propyloxy | 170 | 1200 | +59 | +16 | −27 |
| R′ = isobutyryl | | | | | |
| R″ = isobutyloxy | 270 | 1300 | +69 | +18 | −29 |
| R′ = butyryl | | | | | |
| R″ = methoxy | 80 | 1000 | +69 | +25 | −28 |
| R′ = acetoacetyl | | | | | |
| R″ = isopropyloxy | 295 | 1800 | +67 | +20 | −25 |

[a] values in control animals: 5-HT $\mu g \cdot g^{-1}$ = 732 ± 18, 5-HIAA $\mu g \cdot g^{-1}$ = 430 ± 7.5. N = 10

The compounds of the present invention are orally or parenterally administered, in any of the usual pharmaceutical forms which are prepared by conventional procedures well-known to those persons skilled in the pharmaceutical technology. These forms include solid and liquid oral unit dosage forms such as tablets, capsules, solutions, syrups and the like as well as injectable forms, such as sterile solutions for ampoules and phials.

For these pharmaceutical forms the usual solvents, diluents and excipients are used. Optionally, sweetening, flavoring and preservative agents can also be present. Non limiting examples of such agents are sodium carboxymethylcellulose, polysorbate, mannitol, sorbitol, starch, avicel, talcum and other agents which will be apparent to those skilled in the pharmaceutical technology.

The dose which is administered will be determined by the attending physician having regard to the age, weight and general conditions of the patient, utilizing sound professional judgement. Although effective results can be noticed at doses as low as 5 to 8 mg/kg of body weight dayly, a dose of from about 10 to about 50 mg/kg of body weight is preferred. Whenever necessary, larger doses can be safely administered in view of the low toxicity of the compounds of this invention.

As non-limiting examples and depending on the specific pharmaceutical form of administration, the following dosages can be indicated:

| for the phials | from 5 to 500 mg |
| for the capsules | from 15 to 50 mg |
| for the tablets | from 15 to 500 mg |
| for the oral solutions | from 15 to 50 mg. |

What is claimed is:

1. Esters of acyl-carnitines represented by the general formula (I):

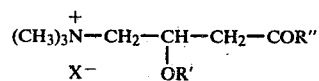

X is halogen;

R′ is: acetyl; halogen-substituted acetyl isobutyryl; β-hydroxy butyryl; acetoacetyl; pantothenyl and linoleyl; and R″ is: methoxy, ethoxy, propyloxy, butyloxy, isopropyloxy, isobutyloxy, trichloroethyloxy, trifluoroethyloxy, 3-carbethoxy-2-propyloxy, 3-pyridyl-methoxy, 2-diethylaminoethoxy, 2-acetamido-3-methyl-butyroxy, 2-acetamido-4-methyl-penthyloxy, 2-acetamido-3-methyl-pentyloxy and 4-hydroxymethyl-5-hydroxy-6-methyl pyrid-3-yl methoxy radicals provided that when R″ is methoxy, ethoxy, propyloxy or butyloxy then R′ is not acetyl.

2. A method of treating depression comprising administering to a patient afflicted by depression an ester of formula (I) as defined in claim 1 in an amount effective in the treatment of depression.

3. An ester according to claim 1, wherein said halogen-substituted acetyl is chloro-acetyl, dichloro-acetyl or bromo-acetyl; said halogen-substituted propionyl is bromopropionyl and said halogen-substituted butyryl is chlorobutyryl.

4. An orally or parenterally administrable pharmaceutical composition for the treatment of myocardial hypocontractility, depressions and disturbed sleep, which comprises a therapeutically effective amount of an ester of formula (I) as defind in claim 1 and a pharmacologically acceptable excipient.

5. A composition according to claim 4 in unit dosage from which comprises from about 5 to about 500 mg of said ester of formula (I).